United States Patent [19]

Matner

[11] Patent Number: 5,137,812

[45] Date of Patent: Aug. 11, 1992

[54] COLONY BLOTTING METHOD AND DEVICE

[75] Inventor: Richard R. Matner, St. Paul, Minn.

[73] Assignee: Minnesota Mining and Manufacturing Company, St. Paul, Minn.

[21] Appl. No.: 742,270

[22] Filed: Aug. 7, 1991

Related U.S. Application Data

[63] Continuation of Ser. No. 401,309, Aug. 31, 1989, abandoned.

[51] Int. Cl.$^5$ .......................... C12Q 1/10; C12Q 1/02; C12Q 1/70; G01N 33/53
[52] U.S. Cl. .......................................... 435/38; 435/4; 435/29; 435/299; 435/34; 435/300; 435/301; 435/293; 435/7.37; 435/7.32
[58] Field of Search ....................... 435/4, 29, 299, 34, 435/300, 301, 293, 7.37, 38, 7.32

[56] References Cited

U.S. PATENT DOCUMENTS

| | | | |
|---|---|---|---|
| 4,539,256 | 9/1985 | Shipman | 428/315.5 |
| 4,565,783 | 1/1986 | Hansen et al. | 435/299 |
| 4,726,989 | 2/1988 | Mrozinski | 428/315.5 |

OTHER PUBLICATIONS

Kemp et al. (1981) Detection of Expressed Polypeptides by Direct Immunoassay of Colonies, Methods in Enzymol. 79:622-630.
S. Broome et al., "Immunological Screening Method to Detect Specific Translation Products", Proc. Natl. Acad. Sci. U.S.A., vol. 75, No. 6, pp. 2746-2749 (1978).
Renart, J. and I. V. Sandoval, "Western Blots", *Methods in Enzymol.*, Chapt. 33, vol. 104, Acad. Press (1984).
Pyle, S. W. and W. B. Schill, "Rapid Serological Analysis of Bacterial Lipopolysaccharides by Electrotransfer to Nitrocellulose", *J. Immunol. Meth.*, 85:371-382 (1985).
Riley, "The Epidemiologic, Clinical, and Microbiologic Features of Hemorrhagic Colitis", *Ann. Rev. Microbiol.*, 41:383-407 (1987).
Doyle et al., Applied and Environmental Microbiology, 53(10):2394-2396 (1987).
Todd et al., Applied and Environmental Microbiology, 54(10):2536-2540 (1988).
Grunstein et al., *Proc. Nat. Acad. Sci. U.S.A.*, 72(10):3961-3965.
Burnette, *Anal. Biochem.*, 112:195-203 (1981).
Hawkes et al., *J. Anal. Biochem.*, 119:142-147 (1982).
Wetherell et al., Amer. Soc. Microbiol. 88th Annual Meeting, Session No. 115, Abstract No. C134 (1988).
Kiley et al., *Inf. Imm.*, 30:862 (1980).

*Primary Examiner*—Christine Nucker
*Assistant Examiner*—David R. Preston
*Attorney, Agent, or Firm*—Gary G. Griswold; Walter N. Kirn; Jennie G. Boeder

[57] ABSTRACT

A method and article for the identification of colonies of microbes involves the use of a reconstitutable dry culture medium plate in combination with a transfer membrane. Microbe-specific antigen can be extracted from the surface of the growth medium of the plate and its presence determined, e.g., by immunoassay.

11 Claims, No Drawings

COLONY BLOTTING METHOD AND DEVICE

This is a continuation of application Ser. No. 07/401,309, filed Aug. 31, 1989, now abandoned.

TECHNICAL FIELD

The present invention relates to the field of colony blotting, i.e., the use of materials such as films or membranes to transfer biological materials from the surface of a streaked (or spread) and incubated culture plate having exposed colonies, for purposes such as biochemical or immunochemical assays. In another aspect the invention relates to the field of immunoblotting generally, and in particular immunoblotting of antigens such as lipopolysaccharides. In another aspect the invention relates to methods for the detection of pathogenic microbes such as the strain designated *Escherichia coli* O157:H7.

BACKGROUND OF THE INVENTION

The blotting of electrophoretically separated biological molecules onto solid supports has been used for a variety of purposes, including to perform immunoassays of the blotted molecules. The "Western blot" is perhaps one of the best known approaches in this respect, which allows the identification of separated and then blotted proteins by the use of antibody probes of the solid support. See generally, Renart, J. and I. V. Sandoval, "Western Blots", *Methods in Enzymol.*, Chapt. 33, Vol. 104, Acad. Press. (1984).

In addition to proteins and polysaccharides, lipopolysaccharides have also been identified by transfer techniques. See, e.g., Pyle, S. W. and W. B. Schill, "Rapid Serological Analysis of Bacterial Lipopolysaccharides by Electrotransfer to Nitrocellulose", *J. Immunol. Meth.*, 85:371-382 (1985).

Another technique, known as "colony blotting", generally involves the transfer of biological molecules from the surface of a culture plate, such as an agar plate having bacterial colonies on its surface, to a solid support. See, for instance, Kemp, D. J. and A. F. Cowman, "Detection of Expressed Polypeptides by Direct Immunoassay of Colonies", in *Methods in Enzymol.*, Chapt. 83, Vol. 79, Acad. Press. (1981), describing a process in which the colonies are first lysed. The proteins released from the lysed cells are then bound covalently to CNBr paper and detected by reaction with radiolabeled antibodies.

Colony blotting is not generally used with pour plate type culture media, where a majority of the colonies are not accessible at the surface of the media, nor has it been described previously for use with reconstitutable dry culture media such as those described more fully below.

By virtue of the time, effort, expertise, and cost required, immunochemical identification of microbes as described above is typically used in the context of the research laboratory as opposed to its use for routine high volume screening of samples for the presence of microbes such as screening done in the food, cosmetic, and drug industries, or for environmental purposes.

In contrast, such routine, high volume screening of samples for the presence of microbes is still typically carried out by laborious and/or relatively insensitive biochemical or microbiological techniques. These techniques often involve whole cell counts and/or the use of preenrichment broth culture followed by selective agar plates. Such techniques generally result in either a simple quantitative answer regarding the total microbial count, or a qualitative (e.g., positive/negative) answer regarding the presence of a particular microbial species of interest. Current rapid screening techniques are rarely if ever able to provide both an indication of the presence of a particular microbe as well as an indication of the concentration of the microbe, let alone allow the user to then locate and isolate the identified microbe, e.g., for further growth and characterization.

A good example highlighting the need for better screening methods is that of the prevalence in meat samples of the pathogenic *E. coli* strain identified as "O157:H7". See, e.g., Riley, "The Epidemiological, Clinical, and Microbiological Features of Hemorrhagic Colitis", *Ann. Rev. Microbiol.* 41:383-407 (1987), the disclosure of which is incorporated herein by reference. Among the tests described as useful for the detection of *E. coli* O157:H7 are those described by Doyle et al., *Applied and Environmental Microbiology*, 53(10):2394-2396 (1987), and Todd et al., *Applied and Environmental Microbiology*, 54(10):2536-2540 (1988), the disclosure of each of which are incorporated herein by reference.

The meat industry currently relies, in large part, on the method of Doyle cited above. This method is basically an enrichment procedure in which samples are grown in a preenrichment broth, diluted, and grown on selective agar in an attempt to visually identify *E. coli* O157:H7 colonies from among the colonies of non-pathogenic background cells. This method suffers from a number of drawbacks, including the need to visually distinguish colonies of *E. coli* O157:H7 from other colonies. Given the typically large number of non-pathogenic bacteria present it is very possible that *E. coli* O157:H7 cells are missed, thereby leading to an undesirably high number of false negatives.

In view of the fact that the U.S. Food and Drug Administration ("FDA") and others are becoming increasingly concerned with the need to identify and quantitate microbial pathogens in samples such as food, combined with the fact that food industry needs a method that is quick, sensitive, cost effective, and practical, the presently available research-oriented techniques are not suitable for such purposes.

SUMMARY OF THE INVENTION

The present invention provides a method for identifying, and optionally locating, the presence of colonies of microbes, the method comprising the steps of:

(1) inoculating a reconstitutable dry culture medium plate with an inoculum from a sample suspected of containing microbes, (2) incubating the inoculated plate under conditions suitable to allow the growth of colonies of the microbes, (3) exposing a surface of the growth medium of the plate and contacting the exposed surface with a suitable transfer membrane in a manner that allows the membrane to extract microbe-specific antigen from the area of the microbial colonies, (4) removing the transfer membrane from the surface of the medium, and (5) determining the presence of microbe-specific antigen on the transfer membrane by suitable means.

The present invention also provides an article of manufacture that includes a reconstitutable dry culture medium plate in combination with a transfer membrane.

In its preferred embodiment the method and article of the present invention are used to detect lipopolysaccharide antigen that is produced by and specific for the microbes. Also, in its preferred embodiment, the method avoids the need to affirmatively lyse the cells of the colonies prior to extraction, as well as the need to block the transfer membrane after extraction in order to prevent unwanted non-specific binding of antibody. Since a lysing step and/or a blocking step are generally necessary in conventional colony blotting, it can be appreciated that the present invention is particularly convenient.

In addition the present invention allows for the screening of substantially all colonies present on the growth medium simultaneously, as opposed to the need to pick a representative number of colonies from selective agar plates for further confirmation or characterization. Given the fact that a plate of the present invention is more analogous to a pour plate medium than a surface-streaked or surface-spread medium, it is particularly surprising, though essential, that antigens of substantially all colonies grown on such a plate are accessible for extraction from the surface of the growth medium of the plate. The present invention also allows the user to locate the original colony of microbes on the surface of the plate, thereby allowing the further isolation and characterization of the colony.

The method and device of the present invention are particularly useful for microbial screening that needs to be performed with specificity but also in an inexpensive and rapid manner for a large number of samples, such as in the commercial dairy, food, water, cosmetic, and drug industries.

DETAILED DESCRIPTION

The method of the present invention involves generally the steps of inoculating a reconstitutable dry culture medium plate with a sample suspected of containing microbes; incubating the inoculated plate; contacting a transfer membrane to the surface of the growth medium of the incubated plate in order to extract microbe-specific antigen therefrom; removing the transfer membrane; and determining the presence, and optionally location, of microbe-specific antigen on the transfer membrane.

The steps will be described in greater detail with respect to a preferred embodiment of the present invention, i.e., in which the method avoids the need to lyse the microbial cells prior to extraction and also avoids the need to "block" the transfer membrane prior to antigen detection. In the particularly preferred embodiment described below the transfer membrane is prepared from polystyrene film; the microbe of interest is the strain designated *E. coli* O157:H7; and the antigen detected is a lipopolysaccharide specific for the *E. coli* serotype O157.

As an initial step in the method of the invention a reconstitutable dry culture medium plate is rehydrated with an inoculum from a sample suspected of containing the microbes of interest.

Suitable media for use in the invention are those that provide an optimal combination of such properties as ease of use, rapid growth of the microbe of interest, selectivity, and cost. A medium should allow the extraction of antigen from its surface in a manner that retains the dimensional and structural integrity of the medium, thereby enabling the later location and isolation of colonies.

Examples of preferred media are described in U.S. Pat. No. 4,565,783, and copending U.S. application Ser. No. 354,627, filed May 19, 1989, the disclosures of both of which are incorporated herein by reference. Dry culture media of these types are presently sold by the 3M Company under the tradename "Petrifilm TM". Preferred dry culture media plates for use in detecting *E. coli* O157:H7 are coliform selective media plates such as Petrifilm TM Coliform Count Plates, and more preferably those known as Petrifilm TM *E. coli* Count Plates. Petrifilm TM plates can be inoculated with an aqueous sample, and thereby rehydrated, according to the manufacturer's instructions.

Dry culture media plates of this sort are further preferred, since in the presently preferred embodiment a cover sheet provides an atmospherically closed environment for the medium. The closed nature of the medium allows any gases that are released by microbes, such as the gases typically released by coliforms, to form a visible bubble around each colony. Applicant has found that the closed nature of the medium, combined with the polar and nonpolar nature of antigens such as LPS, allows the antigen to concentrate at the interface between the medium and the gas, leading to a characteristic circular readout that can be readily and visually detected according to the preferred method of this invention.

Suitable samples for use in the method of the present invention include, but are not limited to food, water, chemical, air, and/or environmental samples. The quantity of sample needed varies depending, for example, upon the sensitivity required and the type of medium to be inoculated. For example, to obtain a sensitivity of less than 1 cell per 100 g of sample, it is generally necessary to test at least 100 g and preferably 500 g of sample in order to obtain a statistical guarantee of less than 1 cell per 100 g of sample. Samples can be tested in a variety of ways familiar to those skilled in the art, e.g., they can either be diluted, (for instance 1/10, 1/100, and so forth) with an appropriate growth medium or buffer, and homogenized for the purpose of pre-enrichment, or they can be used directly to inoculate the culture medium, e.g, as a water or milk sample or a food rinse. Environmental surface samples can be obtained by swabbing a surface area, rinsing the swab in an appropriate growth medium for the purpose of preenrichment or in sterile water or buffer to apply directly to the culture medium.

Samples that are not diluted or that have been diluted and homogenized in an appropriate growth medium or buffer can be pre-enriched in any suitable manner, e.g., grown prior to inoculation, in order to increase microbial cell number. For example, when detecting *E. coli* O157:H7, samples can be prepared by diluting a food sample, e.g., on the order of 1 to 10 (weight to volume), in an appropriate liquid growth medium and incubating with or without shaking for between 4 and 24 hours, preferably between 6 and 8 hours, at temperatures from 20° C. to 44° C., preferably from 32° C. to 42° C. and most preferably at 36° C.

Following preenrichment, an inoculum of sample is used to inoculate a culture medium, e.g., rehydrate a dry culture medium plate such as Petrifilm TM dry culture medium plate, in a conventional manner.

Inoculated culture media are incubated under conditions suitable to allow the growth of colonies of the microbes of interest. For example, rehydrated Petrifilm TM plates are incubated for 6 to 24 hours, preferably from 18 to 24 hours, at temperatures from 20° C. to 44° C., preferably from 36° C. to 42° C., and most preferably 42° C.

Following incubation a surface of the growth medium of the plate is exposed, e.g., by pulling back the transparent cover sheet of the plate, and the exposed surface is contacted with a suitable transfer membrane in a manner that allows the membrane to extract microbe-specific antigen from the medium in the area of the colonies of microbes.

Suitable transfer membranes can be of any suitable form, e.g., film-like, fibrous, or microporous, and of any suitable material, e.g., organic or inorganic. Suitable transfer membranes exhibit an optimal combination of such properties as binding capacity, strength and dimensional stability, hydrophobicity, configuration, and color. Suitable transfer membranes include, but are not limited to, those that are capable of adsorbing proteins, lipoproteins, and lipopolysaccharides. Examples of suitable transfer membranes are prepared using the polymers polypropylene, polyethylene, polystyrene, nitrocellulose, or nylon.

The thickness of a transfer membrane is not critical so long as the membrane is of a suitable thickness for its intended purpose. Typically transfer membranes are on the order of 1 mil to 10 mil thick, and preferably on the order of 1 mil to 5 mil thick.

Preferred transfer membranes for use with hydrophobic antigens such as lipopolysaccharides are generally those that are hydrophobic themselves. A convenient indication of the hydrophobic nature of a membrane is the water absorption of the membrane, e.g., as determined by ASTM Test Method D-570, the disclosure of which is incorporated herein by reference. According to this method preferred membranes for use with LPS antigens exhibit water absorption on the order of 1% (w/w) or less, and most preferably on the order of 0.1 % or less.

Particularly preferred transfer membranes for use with LPS extraction are prepared from polystyrene, polypropylene, or polyethylene. Preferred are microporous polyethylene and polypropylene membranes as described in U.S. Pat. No. 4,539,256, the disclosure of which is incorporated herein by reference. Preferred polystyrene transfer membranes are prepared from a film available under the tradename "Opticite TM #520 Label Film" from Dow Chemical Co. This film is described as containing polystyrene and a styrene/butadiene copolymer at a total polymer content of 80%, together with titanium dioxide, and can be preferably obtained as a 2.5 mil (metric 63.5 μm) thick sheet. The film can be cut into the desired shape, e.g., in a circular shape of substantially the same dimensions as the surface of the growth medium used.

Using Petrifilm TM plates, extraction generally requires the separation of the top cover sheet to expose the surface of the growth medium. The transfer membrane can be contacted with the exposed surface in any suitable manner in order to extract antigen from the surface of the medium. In a preferred embodiment of the invention, extraction of LPS by the transfer membrane from the surface generally occurs instantaneously, i.e., the transfer membrane can be laid over the medium such that it substantially contacts the entire surface thereof, and is then immediately removed. Optionally the membrane can be left in contact with the surface for longer time intervals without adverse effect. The membrane is preferably oriented with the medium, e.g., in a radial fashion, so that it can later be re-aligned with the membrane in order to localize specific colonies. Orientation can be accomplished in any suitable manner, e.g., by marking or nicking both the membrane and the medium.

Prior to extraction it may be necessary to release antigens from cells into the medium, e.g., by exposing the microbial colonies in the medium to a physical, chemical, or biological agent. Suitable releasing agents include, but are not limited to, organic solvents such as chloroform, detergents such as sodium dodecyl sulfate, chelating agents such as EDTA, or enzymes such as a lysozyme which would lyse the cells and release intracellular antigens. See, e.g., Grunstein, et al., *Proc. Nat. Acad. Sci. USA*, 72(10):3961–3965 (1975), the disclosure of which is incorporated herein by reference. For antigens that are extracellular in nature it has been found that very often a lysing step is not needed before extraction.

The transfer membrane can be removed from the surface of the culture medium by any suitable means, e.g., by lifting with tweezers taking care not to reexpose the membrane to the surface or to enzyme-carrying surfaces such as bare fingers. The membrane is preferably washed sufficient times under suitable conditions in order to remove extraneous foreign material. For non-water absorbing, hydrophobic transfer membranes such as those prepared from polypropylene, polystyrene, and polyethylene, three washes in a wash solution containing a small amount of detergent, e.g., Tween 20 or Tween 80, buffered to neutrality is sufficient. For more hydrophilic membranes, up to 10 wash cycles in wash solution may be needed to remove adhered or entrapped extraneous material.

After extraction by the transfer membrane but prior to determination of the presence of extracted antigen on the membrane the user can optionally block the membrane in order to remove remaining sites that could non-specifically bind subsequent reagents such as antibodies. Blocking may be accomplished, for example, by incubation of the transfer membrane in a solution of gelatin, albumin, or rehydrated dried milk at a concentration of on the order of 0.1% to 10%, and preferably 0.5% to 5% (weight to volume). See, e.g., Burnette, *Anal. Biochem.*, 112:195–203 (1981), the disclosure of which is incorporated herein by reference. Preferred transfer membranes do not generally require a blocking step since antibodies will not tend to bind non-specifically to the membranes.

The word "antigen", as used herein, shall refer to any detectable biological macromolecule, e.g., specific binding partner, capable of being extracted from an incubated plate by a transfer membrane from the area of a microbial colony in the manner of the present invention. The word "extract", as used herein, refers to the removal of antigen from the medium to the membrane, e.g., by direct contact leading to binding by passive adsorption, ingestion of medium by capillary action, or the like. Suitable antigens include, but are not limited to, those that are substantially protein, lipoprotein, or lipopolysaccharide in nature. Preferred antigens are present in the extracellular area of a microbial colony, and are either entirely hydrophobic or at least have a hydrophobic region capable of allowing the antigen to be quickly extracted by the surface of a hydrophobic transfer membrane. When both of these factors are met, it has been found that the antigen can often be extracted without lysing the colony and then detected without blocking, as previously described. Preferred antigens include surface LPS's and toxins of pathogenic microbes. An example of a particularly preferred antigen is the LPS antigen identified as the "O-antigen" from *E. coli* serotype O157:H7.

Antigen extracted by the transfer membrane can be determined, e.g., assayed or otherwise detected, by any appropriate means using conventional techniques. See, e.g., Hawkes, et al., *J. Anal. Biochem.*, 119:142–147 (1982), the disclosure of which is hereby incorporated by reference. Suitable techniques include, but are not limited to, incubating the membrane with specific enzyme-, radioactive-, chemiluminescent-, or fluorescent-labeled antibodies. Suitable specific antibodies will bind to the antigen on the transfer membrane, and their presence and location in turn can be detected in an appropriate manner, e.g., by use of appropriate substrate systems such as phosphatase or peroxidase substrate systems for phosphatase- or peroxidase-labeled antibodies.

In a preferred embodiment LPS/antibody complexes can be located on the transfer membrane by radiometric, enzymatic, chemiluminescent, or fluorescent assay systems. Preferably, enzyme labeled anti-LPS antibodies are used to detect LPS extracted by the transfer membrane. Most preferably, phosphatase-labeled anti-*E. coli* O157 polyclonal or monoclonal antibodies are used to detect *E. coli* O157 LPS on the transfer membrane.

Antibody specific for *E. coli* O-antigen can be made by known techniques such as affinity purification as described in Wetherell, et al., Amer. Soc. Microbiol. 88th Annual Meeting, Session No. 115, Abstract No. C134 (1988), or is commercially available, e.g., as Cat. No. 05-95-90 "BacTrace Affinity Purified Antibody to *E. coli* O157:H7" from Kirkegaard and Perry Laboratories, Inc., Gaithersburg, Md., or *E. coli* anti-O157, Cat. No. 2970-47-7, Difco Laboratories, Detroit, Mich.

A particular advantage of the preferred embodiment of the present invention involves the ability to isolate actual cells from colonies of the identified microbe on the original plate itself. By proper orientation of the membrane and plate the user can locate the presence of microbial colonies on the plate by correlating their location with the antigen found on the transfer membrane. The located colonies can then be used, e.g., isolated in a conventional manner, in order to confirm their identity or for any other purpose.

Frequently substantial growth of background microbes will occur in the area of desired colonies, particularly when using highly contaminated samples. In such cases, the desired colonies may not be visually distinguishable. By virtue of the present invention however, determination of antigen specific for such colonies can be used to locate the areas of media that presumptively include the colonies. These areas can be recovered and the desired microbes separated and purified from the background microbes according to known techniques, or by re-inoculation according to the method of the present invention.

An article of the present invention, namely, a reconstitutable dry culture medium plate in combination with a transfer membrane, can be provided in any suitable form. The plate and membrane can be combined, e.g., as component parts of a kit. Optionally the kit can also contain other components, such as antibody and/or substrate useful for the determination of the presence of antigen on the membrane. In such an embodiment the membrane is contacted with an exposed surface of the medium of the plate by the user in the course of the method of the invention.

Alternatively the plate and membrane can be combined as component parts of a unitary structure, e.g., wherein the membrane forms a layer of the plate and is present in contact with the medium throughout the course of inoculation and growth. The membrane can be later removed from the medium surface in order to allow the determination of antigen extracted. For instance, the use of a transfer membrane as the cover sheet itself, or on the underside of such a cover sheet, provides the requisite contact between the medium and the membrane.

The invention is further illustrated by the following EXAMPLES, but the particular materials and amounts thereof recited in these EXAMPLES, as well as other conditions and details should not be construed to unduly limit this invention.

EXAMPLES

EXAMPLE 1

Use of Method with Inoculated Plates

Reconstitutable dry culture medium plates (Petrifilm ™ *E. coli* Count Plates, 3M Company, St. Paul, Minn.) were each inoculated with 1 ml aliquots of a mixed culture containing a laboratory strains of a non-pathogenic *E. coli*, *a Citrobacter*, and a *Klebsiella*. Total bacteria numbered approximately 200 per ml. Approximately 10 *E. coli* O157:H7 were included in each inoculum. Plates were incubated at 32° C. for 18 hours.

The incubated plates were blotted with transfer membranes at room temperature in the following manner. The top film of each plate was pulled back to expose the medium surface.

For some plates a circle-shaped nitrocellulose filter (64 mm diameter, Nytran ™ plain white nitrocellulose, Cat. #BA85, available from Schleicher and Schuell, Inc., Keene, N.H.), was laid over the medium for one minute. For other plates a polypropylene membrane, as described below in EXAMPLE 5, was laid over exposed media surfaces. The filters were removed from the medium, placed in a 250 ml beaker, and washed in excess buffer ("PBS-Tween", phosphate buffered saline containing 0.1% Tween 20, pH 7.4). The buffer was poured off and 1 ml skim milk was added to the beaker containing the nitrocellulose filter in order to block remaining binding sites on the membrane. The polypropylene membranes were not blocked.

Each filter was washed three times in excess PBS-Tween and covered with 2 ml of alkaline phosphatase labeled anti-O157:H7 antibody (containing approximately 0.2 micrograms antibody, KPL Laboratories) for 30 minutes. The antibody was a polyclonal preparation known to be specific for LPS of *E. coli* O157. The antibody solution was poured off and the filter washed as above with PBS-Tween for 30 minutes. Phosphatase substrate (2 ml, reconstituted, KPL Laboratories) was added and incubated with the filter for 5 minutes. The filter was then placed in excess deionized water in order to stop the enzymatic reaction.

Approximately 10 distinctive black circles were apparent on each of the nitrocellulose filters and on the polypropylene discs, indicating that the *E. coli* O157:H7 had grown in its distinctive circular, gas-forming pattern on the plate, and that LPS of that strain was able to be extracted and detected according to the method of this invention. The use of nitrocellulose is not preferred however since the filters each exhibited an overall blue-black tint, indicating non-specific of antibody, and required the additional step of blocking the membrane in order to prevent non-specific binding of labeled antibody. In contrast, there was no overall background tint on the polypropylene discs, even though they had not been similarly blocked.

EXAMPLE 2

Use of Method with Hamburger Samples

Fifty raw hamburger and cooked hamburger samples, inoculated with *E. coli* O157:H7, were tested by the Doyle enrichment method cited previously and by the method of the present invention according to the protocol below. Of raw hamburger samples inoculated with O157:H7, 19 were detected by the method of the present invention in 24 hours. The Doyle conventional enrichment method failed to detect any positives in the 20 samples after 3 days. Presumably, the conventional method failed due to background overgrowth. Both methods detected 20 out of 20 inoculated cooked hamburger samples. The conventional method required 3 days while the method of the present invention required 24 hours.

It appears that the method of the present invention can detect on the order of one *E. coli* O157:H7 cell per 10 grams of raw hamburger if the initial background gram-negative count is less than about $10^4$ per gram. The sensitivity increases to 1 *E. coli* O157:H7 cell per 50 grams of raw hamburger if the initial count is less than about $10^3$ per gram. For precooked hamburger, clearly, the sensitivity is even greater.

PROTOCOL

Reagent Preparation

1) Anti-O157:H7 affinity purified polyclonal IgG (100 µg, KPL, Inc., Gaithersburg, Md., Cat. #05-95-90) was rehydrated with 1 ml of 50% glycerol and stored at −20° C.

2) "BCIP/NBT" substrate system (KPL, Inc.) was prepared using 10 parts buffer (0.1 M Tris, pH 9.0)+1 part 5-bromo-4-chloro-3-indolyl phosphate ("BCIP")+1 part nitroblue tetrazolium ("NBT") made up just prior to use.

3) Wash solution was prepared using a 25 ml wash solution concentrate (0.5 M Tris, 4.8 M NaCl, 2% Tween 20) added to one liter distilled water, pH to 7.2.

Analysis

1. Dilute 25 g sample hamburger 1/10 (weight/volume) into 225 ml modified trypticase soy broth "mTSB" preenrichment broth prepared using the following ingredients:

30 g trypticase soy broth "TSB":BBL (Microbiological Systems, Cockeysville, Md.)

1.5 g bile salts "#3" (Difco Laboratories, Detroit, Mich.)

1.5 g dipotassium phosphate 20 mg novobiocin (Sigma Chemical Co., St. Louis, Mo.)

pH 7.4, and homogenize for 30 seconds.

2. Transfer homogenate into a 500 ml flask and incubate for 6-8 hours at 36° C. with shaking (60 gyrations per minute).

3. Inoculate duplicate Petrifilm™ *E coli* Count plates with 1 ml preenrichment or 1 ml of a 1/10 dilution of incubated preenrichment broth.

4. Incubate for 18-24 hours at 42° C.

5. Expose the medium surface of the Petrifilm™ plate by peeling apart the top and bottom films. Place the transfer membrane in contact with the exposed medium surface so that transfer membrane contacts the entirety of the medium surface and no air bubbles are left between the medium and the membrane. Mark transfer membrane and medium accurately for future orientation.

6. Remove transfer membrane and place in beaker in excess wash solution, contacted side down. Alternate membranes and inert mesh spacer when batching, beginning with mesh spacer at the bottom of beaker. Swirl beaker. Pour off wash solution. Repeat and ensure that excess residual medium does not stick to membrane.

7. Pour off wash solution. Add 4 ml per membrane new wash solution and 2 µl per membrane of anti-O157:H7 antibody solution.

8. Incubate for 30 min. at room temperature with swirling (60 gyrations per minute), to ensure that membranes do not adhere to each other.

9. Pour off antibody solution. Rinse in wash solution (approximately 10 ml per membrane). Swirl beaker. Pour off wash solution. Repeat twice.

10. Add 2 ml substrate per membrane to beaker.

11. Incubate for 5 min., with moderate swirling to ensure that membranes do not adhere to each other.

12. Rinse membranes in tap water to end reaction.

13. Remove membranes from beaker and blot dry.

Recovery and Confirmation of Presumptive O157:H7 Colonies

14. Use a pasteur pipette on a padded surface to mark and remove spots on transfer membrane. This is most easily done using a twisting motion as the pipette is pressed downward, pulling straight upward to remove the spot.

15. Align marking on membrane and film by placing the membrane on top of the film. With felt tipped marker, lightly touch top film inside the punched hole.

16. Carefully lift top film and lay flat. Using a Prompt™ inoculation system wand (BBL Microbiological Systems, Cockeysville, Md.), touch medium where marker spot shows through. Twist slightly and pull straight up to remove medium. Repeat for a maximum of 3 spots per wand.

17. Break open 1 ml bottle of Prompt™ inoculation system bottle (BBL Microbiological Systems, Cat. No. 26306, Cockeysville, Md.) and place wand inside. Vortex 60 sec. to adequately dispense microbes from wand into solution.

18. Using a "hockey stick"-type bacterial transfer device, plate 100 µl, and 1 µl Prompt solution onto 3 "MSA" plates (prepared using 22.2 g MacConkey Agar base with 10 g D-sorbitol made up to 1 liter with water). Spreading of the 1 µl and 10 µl samples can be facilitated by adding 100 µl sterile water to the plate.

19. Incubate MSA plates at 42° C. for 18-24 hrs.

20. Test suspect colonies for latex agglutination using an "*E. coli* O157 Latex Test", Cat. #DR 620, Oxoid U.S.A., Inc., Columbia, Md.

EXAMPLE 3

Use of Method with Clinical Samples Direct Sample

A double blind clinical study was run using stool samples from an *E. coli* O157:H7 outbreak in a local day care center. Samples were inoculated, incubated, extracted, and detected as described above in EXAMPLE 2, steps 3 through 20 with the exception that the stool samples were diluted 1:10 in PBS and diluted 1:1000 before rehydrating Petrifilm ™ E coli Count Plates with 1 ml of the 1:1000 dilution. As seen below in TABLE I, the method of the present invention correctly identified all positive clinical stool samples submitted (4 out of 15) within 24 hours. In addition, the method quantitated total coliforms and total E. coli, as well as identifying the presence of E. coli O157:H7 in each sample.

In contrast, the samples had been previously analyzed by directly streaking a swab of the stool sample onto an MSA plate, incubating the plates, and testing by the latex agglutination test described above. This approach took far longer than the method of the present invention and was limited in terms of its sensitivity, particularly with samples having high background contamination (e.g., over about 200 coliform per E. coli O157:H7 cell).

TABLE I

Minnesota Daycare Center Outbreak - August 1988

| Sample # | Total Coliforms | Total E. coli | O157:H7 |
|---|---|---|---|
| 720 | $4.3 \times 10^2$/g | $4 \times 10^2$/g | $4 \times 10^2$/g |
| 721 | $1.0 \times 10^1$/g | 0 | 0 |
| 722 | $7.4 \times 10^2$/g | 0 | 0 |
| 725 | $8.2 \times 10^4$/g | $3.0 \times 10^4$/g | $3.0 \times 10^4$/g |
| 726 | $1.2 \times 10^5$/g | $5.1 \times 10^4$/g | $3.4 \times 10^4$/g |
| 727 | $2.3 \times 10^5$/g | $1.5 \times 10^5$/g | $1.5 \times 10^5$/g |
| 728 | $1.8 \times 10^2$/g | 0 | 0 |
| 731 | 0 | 0 | 0 |
| 733 | $1.4 \times 10^4$/g | 0 | 0 |
| 735 | $2.0 \times 10^1$/g | 0 | 0 |
| 737 | $2.3 \times 10^5$/g | $2.2 \times 10^5$/g | 0 |
| 738 | $3.1 \times 10^6$/g | $1.0 \times 10^5$/g | 0 |
| 739 | $3.1 \times 10^4$/g | $2.7 \times 10^4$/g | 0 |
| 740 | $1.7 \times 10^7$/g | $1.7 \times 10^7$/g | 0 |
| 741 | $1.2 \times 10^5$/g | $1.2 \times 10^5$/g | 0 |

EXAMPLE 4

Identification of Antigen as LPS

LPS was isolated from E. coli O157:H7 in the following manner. A single colony of E. coli O157:H7 grown overnight on a standard agar plate (5 g tryptone, 2.5 g yeast extract, 1 g dextrose, 15 g agar, water to 1 liter) was used to inoculate a 2 ml tube of Tryptic Soy Broth (BBL Microbiological Systems, Cockeysville, Md.). The culture was grown for 18 hours at 36° C. The culture was centrifuged at 6000 RPM for 3 minutes to pellet the cells. The supernatant was discarded. Cells were resuspended in 100 μl of 0.01 M phosphate buffered saline, pH 7.2 (1.2 g Na$_2$HPO$_4$, 0.22 g NaH$_2$PO$_4$·H$_2$O, 8.5 g NaCl, H$_2$O to 1 liter). The resuspended cells were heated in a boiling water bath for 2½ hours in order to release and hydrolyze cellular contents. The suspension was centrifuged at 6000 RPM for 3 minutes and the supernatant discarded.

LPS was suspended in 0.01 M phosphate buffered saline with 0.15% bile salts #3, added in order to help solubilize the LPS, at a concentration of 250 ng/ml. 50 microliters of the antigen preparation was spotted onto a transfer membrane ("Opticite ™ #520"). 50 microliters of phosphate buffered saline was spotted onto the same membrane as a control. The membrane was incubated for 10 minutes at room temperature and placed into excess wash buffer in a 250 ml glass beaker. Wash buffer was immediately poured off and 4 ml of new wash buffer containing 200 ng anti-O157:H7 antibody (KPL, Inc.) was added and incubated 30 minutes at room temperature. The antibody solution was poured off and the filter washed 3× in wash buffer. BCIP/NBT substrate solution (2 ml) (KPL, Inc., Gaithersburg, Md.) was added and incubated for 5 minutes at room temperature. Excess deionized water was added to end the reaction. The presence of bound anti-O157:H7 LPS antibody was determined visually by the appearance of blue staining indicative of reaction of the conjugated alkaline phosphatase. No color was apparent at the site of PBS.

LPS was isolated from *Actinobacillus actinomycetemcomitans* ("Aa") strain having American Type Culture Collection Accession No. 29523 as described in Kiley, et al., *Inf. Imm.* 30:862 (1980). LPS was suspended in 0.01 M PBS with 0.15% bile salts #3, added in order to help solubilize the LPS, at a concentration of 250 ng/ml. 50 microliters of the antigen preparation were spotted onto a transfer membrane ("Opticite" #520"). 50 microliters of PBS was spotted onto the same membrane as a control. The membrane was incubated for 10 minutes at room temperature and placed into excess wash buffer in a 250 ml glass beaker. Wash buffer was immediately poured off and 4 ml of new wash buffer containing 200 ng anti-Aa antibody specific for the LPS of Aa was added and incubated 30 minutes at room temperature. The antibody solution was poured off and the filter washed 3× in wash buffer. 4 ml of new wash buffer containing 200 ng of phosphatase-labeled goat anti-mouse IgG (KPL, Inc., Gaithersburg, Md.) was added and incubated 30 minutes at room temperature. The antibody-containing buffer was poured off and the membrane washed twice with excess wash buffer. BCIP/NBT substrate solution (2 ml) prepared as in EXAMPLE 2 was added and incubated for 5 minutes at room temperature. Excess deionized water was added to end the reaction. The presence of bound anti-Aa LPS antibody was determined visually by the appearance of blue staining indicative of reaction of the conjugated alkaline phosphatase. No color was observed at the site of PBS.

EXAMPLE 5

Identification of Suitable Transfer Membranes

E. coli O157:H7 was grown overnight and LPS antigen was isolated as described in EXAMPLE 4 with the exception that the final pellet was resuspended in TSB broth containing 0.1% bile salts #3. Squares of the following transfer membranes, approximately 5 cm×5 cm (2 in.×2 in.) in dimension, were used:

polystyrene - "Opticite", Dow Chemical Co., Granville, Ohio, Cat. Product No. 02455 nitrocellulose - "Nytran", Schleicher and Schuell, Keene, N.H., Cat. #BA85 nylon - "Biodyne A", Pall BioSupport Co., Glen Cove, N.Y., Cat. #BNPGR875 polypropylene (microporous) - prepared using 46.5% polypropylene, 55.3% mineral oil, and 0.2% Millad 3905 nucleating agent as described in Example 9D of U.S. Pat. No. 4,726,989, the disclosure of which is incorporated herein by reference polyethylene (microporous) - prepared using 40% polyethylene and 60% mineral oil according to the method described in Example 8 of U.S. Pat. No. 4,539,256

The pore size of the microporous polypropylene and polyethylene was 0.22 μm and 0.424 μm, respectively, as determined by the bubble point technique described in the '256 patent, and the void volume of each was 63% and 84%, respectively, as also determined by the method described in the '256 patent.

50 microliters of the *E. coli* O157:H7 antigen preparation was spotted onto each membrane. 50 microliters of TSB medium with 0.15% bile salts was spotted onto each membrane as a control. Each membrane was incubated for 10 minutes at room temperature and placed into excess wash buffer in a 250 ml beaker. Wash buffer was immediately poured off and 4 ml of new wash buffer containing 200 ng anti-*E. coli* O157 antibody (KPL, Inc.) was added and incubated for 30 min. at room temperature. The antibody-containing buffer was poured off and the membranes washed twice with excess wash buffer. Phosphatase substrate solution (2 ml) was added and incubated for 5 minutes, after which excess deionized water was added to end the reaction.

The presence of bound anti-O157 antibody was determined visually by the appearance of blue staining indicative of reaction of the conjugated alkaline phosphatase. An overall bluish tint to the entire surface of a particular membrane indicated an undesirably high level of background, e.g., of antibody binding non-specifically to the membrane itself or to non-LPS extracted molecules. The lack of any blue color indicated that no detectable amounts of LPS were extracted by the particular membrane.

As seen in TABLE II below the more hydrophilic membranes, nitrocellulose and nylon exhibited undesirably high levels of background, presumably due to their ability to adsorb great amounts of protein. In contrast, the more hydrophobic polystyrene, polypropylene, and polyethylene membranes used were able to both extract LPS to the apparent exclusion of protein, and to serve as a suitable support for the immunoreaction of such LPS with antibody. In particular, the polystyrene exhibited the highest LPS binding and lowest background color of all transfer membranes tested.

TABLE II

| Transfer Membrane | Assay Result |
| --- | --- |
| polystyrene | no observed background |
| nitrocellulose | very high background |
| nylon | very high background |
| polypropylene | low background |
| polyethylene | low background |

What is claimed is:

1. A method for identifying the presence of colonies of microbes, the method comprising the steps of:
   (1) inoculating a reconstitutable dry culture medium plate comprising (a) a substantially flat self-supporting body member and (b) a cover sheet adhered to at least a portion of the body member, with an inoculum from a sample suspected of containing microbes,
   (2) incubating the inoculated plate under conditions suitable to allow the growth of colonies of the microbes,
   (3) removing the cover sheet to expose a surface of the growth medium of the plate and contacting the exposed surface with a suitable transfer membrane, the transfer membrane provided separate from the cover sheet, in a manner that allows the membrane to extract microbe-specific antigen from the area of the microbial colonies,
   (4) removing the transfer membrane from the surface of the medium, and
   (5) determining the presence of microbe-specific antigen on the transfer membrane by suitable means.

2. A method according to claim 1 further comprising the step of locating the colonies on the surface of the medium by corresponding the location of antigen on the membrane with the location of colonies on the medium.

3. A method according to claim 1 wherein said membrane is hydrophobic.

4. A method according to claim 3 wherein said membrane comprises a polymer selected from the group consisting of polystyrene, polyethylene, and polypropylene.

5. A method according to claim 4 wherein said membrane comprises polystyrene.

6. A method according to claim 1 wherein said microbes are a species of coliform.

7. A method according to claim 6 wherein said microbes are *Escherichia coli*.

8. A method according to claim 7 wherein said microbes are of the serotype *E. coli* O157:H7.

9. A method according to claim 1 wherein said antigen is selected from the group consisting of proteins, lipoproteins, and lipopolysaccharides.

10. A method according to claim 9 wherein said antigen is lipopolysaccharide.

11. A method for identifying the presence of colonies of microbes, the method comprising the steps of:
   (1) inoculating a reconstitutable dry culture medium plate comprising (a) a self-supporting body member, and (b) a cover sheet adhered to at least a portion of the body member, with an inoculum from a sample suspected of containing microbes, wherein the cover sheet is itself suitable, and used, as a transfer membrane,
   (2) incubating the inoculated plate under conditions suitable to allow the growth of colonies of the microbes,
   (3) removing the cover sheet from the surface of the growth medium of the plate in a manner that allows the cover sheet to serve as a transfer membrane to extract microbe-specific antigen from the area of the microbial colonies,
   (4) removing the transfer membrane from the surface of the medium, and
   (5) determining the presence of microbe-specific antigen on the transfer membrane by suitable means.

* * * * *

UNITED STATES PATENT AND TRADEMARK OFFICE
CERTIFICATE OF CORRECTION

PATENT NO. : 5,137,812
DATED : August 11, 1992
INVENTOR(S) : Richard R. Matner

It is certified that error appears in the above-indentified patent and that said Letters Patent is hereby corrected as shown below:

Col. 10, line 51    after "100 $\mu$l," insert --10 $\mu$l,--

Signed and Sealed this

Twenty-sixth Day of July, 1994

Attest:

BRUCE LEHMAN

*Attesting Officer*    *Commissioner of Patents and Trademarks*